United States Patent
Wilz

(10) Patent No.: US 7,306,633 B2
(45) Date of Patent: Dec. 11, 2007

(54) PRE-TREATMENT COMPOSITION FOR OXIDATIVE COLORING KERATIN FIBRES AND PROCESS THEREFORE

(75) Inventor: Ruediger Wilz, Pfungstadt (DE)

(73) Assignee: KPSS-Kao Professional Salon Services GmbH, Darmstadt (DE)

( * ) Notice: Subject to any disclaimer, the term of this patent is extended or adjusted under 35 U.S.C. 154(b) by 324 days.

(21) Appl. No.: 11/086,247

(22) Filed: Mar. 22, 2005

(65) Prior Publication Data

US 2005/0210606 A1    Sep. 29, 2005

(30) Foreign Application Priority Data

Mar. 27, 2004   (EP)   .................... 04007479

(51) Int. Cl.
*A61K 7/13* (2006.01)

(52) U.S. Cl. ............... 8/405; 8/406; 8/425; 8/550; 8/607; 132/208

(58) Field of Classification Search ............ 8/405, 8/406, 425, 550, 607; 132/202, 208
See application file for complete search history.

(56) References Cited

U.S. PATENT DOCUMENTS 6,696,417 B1 *   2/2004   Raghupathi et al. .......... 514/17
2004/0028642 A1 *   2/2004   Hansenne et al. ............ 424/74

OTHER PUBLICATIONS

English abstract of the Patent No. DE 20115892 U1.*

* cited by examiner

*Primary Examiner*—Eisa Elhilo
(74) *Attorney, Agent, or Firm*—Norris McLaughlin & Marcus PA

(57) ABSTRACT

The present invention concerns a pre-treatment composition comprising dihydroxyacetone (DHA) for oxidative coloring keratin fibers especially human hair and a coloring process therefore.

8 Claims, No Drawings

PRE-TREATMENT COMPOSITION FOR OXIDATIVE COLORING KERATIN FIBRES AND PROCESS THEREFORE

The present invention concerns a pre-treatment composition for oxidative coloring keratin fibers especially human hair and a coloring process therefore.

In oxidative hair coloring area affords have always been made to achieve intensive and quick colorations in addition to the trials of reducing hair damage. For example in EP 545 257 A2 potassium iodide is used to realize this.

Furthermore, in WO 88/01161 and WO 88/01162, several metal salts are included in colouring compositions in order to achieve intensive colorations.

Again in EP 642 783 attempts have been made to achieve brilliant and intensive colors by using known ammonium salts in combination with metal salts into oxidative coloring compositions.

Recently, dihydroxyaceton (DHA) is found to be a color intensifier in oxidative hair coloration. Detailed information on this can be found European Patent Applications EP 1250908, EP 1250909, EP 1250910, EP 1250911, EP 1250912 and as well in WO 96/09807. In those applications, DHA is added into the coloring composition.

However, in the case that DHA is added into the oxidative coloring composition, at the end of the coloring process, it becomes obvious that the parts come in contact first with coloring composition (at the beginning of coloring process) is colored differently than the parts come in contact with coloring composition at the end of the process. In other words, the time that DHA is coming in contact with oxidation coloring basis and coupling agents is very important criteria for determining the coloration results. For example, taking the whole head, if a hair dresser starts with coloration from left hand side of head and finalizes the process on right hand side of head, at the end of processing time and after rinsing hair off with water, it becomes obvious that the left hand side is colored darker and/or shade wise differently from the right hand side. This is certainly a big problem as none wishes to have such kind of color differences after such a process.

The current invention starts from the objective to overcome such kind of problems.

Inventor of the present invention have surprisingly found out that in the case that DHA comprising composition is applied onto hair before bringing compositions comprising mixture of oxidation dyestuffs precursors and/or couplers and an oxidizing agent onto hair, hair is homogeneously colored and no color differences are observed between various parts of hair. It should certainly be well understood, that DHA comprising composition can as well be applied onto hair after application of compositions comprising mixture of oxidation dyestuffs precursors and an oxidizing agent. The color result is not being affected by changing the order of application of agents.

Thus, the objective of the present invention is on first of all a composition comprising DHA to be used as aid for oxidative coloring keratin fibers especially human hair in the form of a pre- and/or after-treatment.

Secondly, the present invention is on a process for coloring hair in which a DHA comprising composition is applied first as a pre-treatment and afterwards, without rinsing hair off, coloring composition comprising one or more oxidation dyestuff precursors and/or coupling agents mixed with an oxidizing agents is applied and after appropriate processing time with or without heat application, hair is rinsed off with water and, if necessary, shampooed.

The above process can as well be applied in the opposite order which means, firstly a coloring composition is applied onto hair and DHA comprising composition is homogeneously applied onto hair immediately afterwards (use as after-treatment composition) and after appropriate processing time, hair is rinsed off and, if necessary, shampooed.

The preferred process is the one firstly mentioned above, namely use of DHA comprising composition as a pre-treatment, as using DHA comprising composition after application of coloring composition, so called after-treatment, may extend time needed for homogenously mixing of DHA into the coloring composition on hair in practice.

According to the present invention DHA concentration in the pre- or after-treatment composition is typically from 0.1 to 20%, preferably 0.1 to 15% and most preferably 0.1 to 10% and in particular 0.1 to 7.5% by weight calculated to the total of the composition, excluding coloring and oxidizing compositions. It should be noted here that any concentration is mentioned in the present description is only for pre- or after treatment composition in weight percentages and the total composition does not include coloring and oxidation agents.

It should as well be noted that compositions of the present invention can be prepared just before application by dissolving DHA in the appropriate base, such as water and/or compositions comprising additional cosmetic ingredients (see below), prior to application to hair. In this case, DHA is kept in powder form until application in an appropriate packaging.

As a rule, an aqueous solution, only DHA dissolved in water, is basically appropriate for achieving intensive and homogeneous colorations. Due to wishes in achieving more cosmetic applications and as well more effects or improvements in hair structure especially in terms of combability (specifically in the case of chemically multi-processed hair), bounce, shine, softness, additional cosmetic ingredients are used in pre- or after-treatment compositions of the present invention. Easiness of application is achieved, for example by addition of ingredients improving combing of hair during application and more effective processing time is achieved with compositions having appropriate consistency (viscosity).

The solution of DHA can be thickened with polymers of any kind, namely, anionic, cationic, nonionic and/or ampho-teric polymers. Natural polymers such as chitosan and its derivatives, cellulose and its derivatives and especially hydroxyethylcellulose, guar gum and its derivatives serve excellently for this purpose. The viscosity values targeted should not be very high in any case should not be more than 2000 mPa.s measuered with either Höppler or Brookfield viscosimeter with the known means as explained in the manuals of the respective equipments at 20° C.

Pretreatment composition of the present invention may comprise cationic polymers as thickeners and at the same time conditioning agents which enhances first of all combability and therefore makes applications onto hair easier. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, those cationic polymers known with their CTFA category name Polyquaternium may as well be added into pre-treatment compositions of the present invention. Typical examples of those are Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46.

As well those polymers known with their CTFA category name Quaternium can as well be suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

In this context, reference is also made to the cationic polymers disclosed in DE 25 21 960, 28 11 010, 30 44 738 and 32 17 059, as well as to the products described in EP-A 337 354 on pages 3 to 7, It is also possible to use mixtures of various cationic polymers.

The cationic polymers also include the quaternized products of graft polymers from organopolysiloxanes and polyethyl oxazolines described in EP-A 524 612 and EP-A 640 643.

Suitable non-ionic polymer is first of all vinylpyrrolidon polymers either homopolymers or copolymers with, especially, vinylacetate. Those are known with the trade name "Luviskol" as homopolymers Luviskol K 30, K 60 or K 90 as well copolymers Luviskol VA 55, VA 64 from BASF AG.

Further non-ionic polymer suitable for compositions of the present invention is vinylpyrrolidone/vinylacetae/vinylpropionate copolymer known with the trade name Luviskol VAP 343 as well from BASF.

Amphoteric or zwitterionic polymers may be contained in composition of the present invention. Examples are copolimerisate of n-octylacrylamide, acrylic or metahcrylic acid and tert.-butylaminoethylmethacrylate known with its trade name Amphomer, copolymer of methacryloylethylbetaine and alkyl methacrylate known as Yukaformer, terpolymer of metahcrylic or acrylic acid and itaconoic acid and a basic monomer of mono or dialkylaminoalkyl acrylate or methacrylate or acrylate of methacrylamide known with the trade name Aquaflex SF 40.

As amphoteric polymers which can be used alone or in mixture with at least one additional cationic and/or nonionic polymer, reference is here made in particular to copolymers of N-octyl acrylamide, (meth)acrylic acid and tert.-butyl aminoethyl methacrylate of the type "Amphomer®"; copolymers from methacryloyl ethyl betaine and alkyl methacrylates of the type "Yukaformer®", e.g. the butyl methacrylate copolymer "Yukaformer® Am75"; copolymers from monomers containing carboxyl groups and sulfonic groups, e.g. (meth)acrylic acid and itaconic acid, with monomers such as mono- or dialkyl aminoalkyl (meth)acrylates or mono- or dialkyl-aminoalkyl (meth)acrylamides containing basic groups, in particular amino groups; copolymers from N-octyl acrylamide, methyl methacrylate, hydroxypropyl methacrylate, N-tert.-butyl aminoethyl methacrylate and acrylic acid, as well as the copolymers known from U.S. Pat. No. 3,927,199.

Anionic polymers may as well be contained in compositions of the present invention. Suitable ones are vinyl alkyl ether, in particular methyl vinyl ether/maleic acid copolymers, obtained by hydrolysis of vinyl ether/maleic anhydride copolymers, distributed under the trade name "Gantrez® AN or ES". These polymers may also be partly esterified, as for example, "Gantrez® ES 225" or "ES 435", the ethyl ester of an ethyl vinyl ether/maleic acid copolymer, or the butyl or isobutyl ester thereof.

Further useful anionic polymers are in particular vinyl acetate/crotonic acid or vinyl acetate/vinyl neodecanoate/crotonic acid copolymers of the type "Resyn®"; sodium acrylate/vinyl alcohol copolymers of the type "Hydagen® F", sodium polystyrene sulfonate, e.g. "Flexan® 130"; ethyl acrylate/acrylic acid/N-tert.-butyl acrylamide copolymers of the type "Ultrahold®"; vinyl pyrrolidone/vinyl acetate/itaconic acid copolymers, acrylic acid/acrylamide copolymers or the sodium salts thereof of the type "Reten®"; etc.

According to the present invention concentration of polymers of anionic, cationic, non-ionic and/or amphoteric or zwitterionic character is in the range of 0.05-10%, preferably 0.05-7.5% and most preferably 0.05-5% by weight in the pre- or after-treatment compositions, calculated to the total composition.

The composition of the present invention can comprise additionally one or more surfactants selected from non-ionic, anionic, cationic and amphoteric ones.

The surfactants suitable for the compositions according to the invention are first of all those nonionic surfactants. Pre-treatment compositions according to the invention comprise one or more nonionic surfactants. Preferred nonionic surfactants are ethoxylated fatty alcohols according to the following formula:

where $R_1$ is a saturated or unsaturated, linear or branched alkyl chain with 12 to 22 C atoms and n is a number between 2 and 50 preferably 2 to 40, more preferably 2 to 30. In one of the prefreed embodiments of the invention, the hair treatment compositions comprise a mixture of two nonionic fatty alcohol ethoxylates, one has between 2 to 10 ethoxylate units and the other is more than 10. Those surfactants are known by the generic terms for example "Laureth", "Myristeth", "Oleth", "Ceteth", "Deceth", "Steareth" and "Ceteareth" according to the CTFA nomenclature, including addition of the number of ethylene oxide molecules. e.g. "Ceteareth-20", Steareth-2, Further nonionic surfactants suitable as emulsifiers in hair treatment compositions according to the invention are those polyethylene glycol ethers of monogylcerides according to the general formula

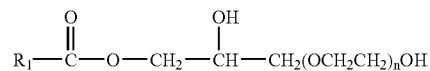

$R_1$ and n are same as above. Examples to those types of nonionic surfactants are PEG-7-glyceryl cocoate known with the trade name Cetiol HE from Cognis, PEG-8-glyceryl laurate know with the trade name Glycerox L8 from Croda Chemicals, PEG-10 glyceryl oleate, PEG-15 glycerryl isostearate, PEG-5 glycerryl stearate, PEG-15 gylceryl ricinoleate, etc.

Further nonionic surfactants suitable for treatment compositions according to the invention are alkyl polyglucosides of the general formula

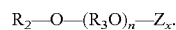

wherein $R_2$ is an alkyl group with 8 to 18 carbon atoms, $R_3$ is an ethylene or propylene group, Z is a saccharide group with 5 to 6 carbon atoms, n is a number from 0 to 10 and x is a number between 1 and 5.

Nonionic surfactant components are, for example, long-chain fatty acid mono- and dialkanolamides, such as coco fatty acid monoethanolamide and myristic fatty acid monoethanolamide, which can also be used as emulsifiers according to the invention.

Additionally useful nonionic surfactants are the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics$^R$", as well as fatty alcohol ethoxylates.

Still further suitable nonionic surfactants are amineoxides. Such amineoxides are known especially because of their use in cleansing compositions, for example $C_{12}$-$C_{18}$-alkyl dimethyl amineoxides such as lauryl dimethyl amineoxide, $C_{12}$-$C_{18}$-alkyl amidopropyl or -ethyl aminoxides, $C_{12}$-$C_{18}$-alkyl di(hydroxyethyl) or (hydroxypropyl) amineoxides, or also amineoxides with ethyleneoxide and/or propyleneoxide groups in the alkyl chain. Those are on the market, for example, under the trade names "Ammonyx®", "Aromox®" or "Genaminox®".

Anionic surfactants of the sulfate, sulfonate, carboxylate types are as well suitable in the pre-treatment composition of the present invention. Those are the ones very commonly used in cosmetic cleansing preparations, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

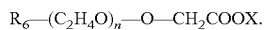

wherein $R_6$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

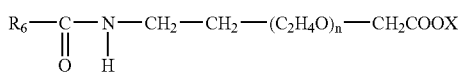

wherein $R_6$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in mixture with other anionic surfactants, as well as sulfofatty acids and the esters thereof.

It is also possible to use mixtures of several anionic surfactants in mixture within the scope of the invention.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N-$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

As further surfactant component, the compositions according to the invention can also contain amphoteric or zwitterionic surfactants as emulsifiers.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

In detail, it is possible to use betaines of the structure

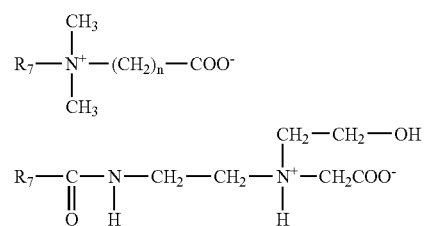

wherein $R_7$ is a $C_8$-$C_{18}$-alkyl group and n is 1 to 3; sulfobetaines of the structure

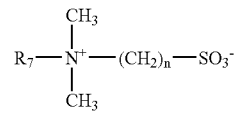

wherein $R_7$ and n are same as above; and amidoalkyl betaines of the structure

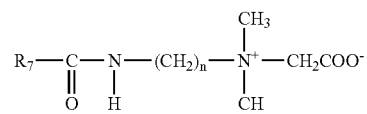

wherein $R_7$ and n are same as above.

Cationic surfactants are useful in the compositions of the present invention as well and particularly as conditioning agents, according to the general formula

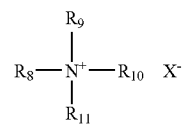

where $R_8$ is a saturated or unsaturated, branched or non-branched alkyl chain with 8-22 C atoms or

where $R_{12}$ is saturated or unsaturated, branched or non-branched alkyl chain with 7-21 C atoms and n has typical value of 0-4 or $$R_{13}COO(CH_2)_n$$

where $R_{13}$ is saturated or unsaturated, branched or non-branched alkyl chain with 7-21 C atoms and n has typical value of 0-4, and $R_9$ is a hydrogen, lower alkyl chain with 1 to 4 carbon atoms, saturated or unsaturated, branched or non-branched alkyl chain with 8-22 C atoms or $$R_{12}CONH(CH_2)_n$$

where $R_{12}$ is saturated or unsaturated, branched or non-branched alkyl chain with 7-21 C atoms and n has typical value of 0-4 or $$R_{13}COO(CH_2)_n$$

where $R_{13}$ is saturated or unsaturated, branched or non-branched alkyl chain with 7-21 C atoms and n has typical value of 0-4, and $R_{10}$ and $R_{11}$ are independent from each other H or lower alkyl chain with 1 to 4 carbon atoms, and X is chloride, bromide or methosulfate.

Suitable cationic surfactants and or conditioning agents are, for example, long-chain quaternary ammonium compounds which can be used alone or in admixture with one another, such as cetyl trimethyl ammonium chloride, myristoyl trimethyl ammonium chloride, trimethyl cetyl ammonium bromide, stearyl trimethyl ammonium chloride, dimethyl stearyl ammonium chloride, dimethyl dihydrogenated tallow ammonium chloride, stear trimonium chloride, dipalmitoyl dimonium chloride, distearyl dimethyl ammonium chloride, stearamidopropyl trimonuim chloride and dioleoylethyl dimethyl ammonium methosulfate, etc.

From the above quaternary ammonium compounds disclosed with the general formula, especially preferred as hair conditioning agents are those compounds known per se and are on the market, for example, under the trade names "Schercoquat®", "Dehyquart® F30" and "Tetranyl®".

Again from the above quaternary ammonium compounds disclosed with the general formula, especially preferred as conditioning ingredient are these compounds are known per se and on the market, for example, under the trade name "INCROQUAT® HO" or "OCS". Those compounds are known with a general ingredient category under "amidoquat" in the cosmetic industry.

According to present invention concentration of surfactants of anionic, cationic, non-ionic and/or amphoteric or zwitterionic character is in the range of 0.05-10%, preferably 0.05-7.5% and most preferably 0.05-5% by weight, calculated to the total composition.

Pre- or after-treatment compositions of the present invention can as well contain other conditioning agents selected from oily substances and nonionic substances. Oily substances are selected from such as silicone oils either volatile or non-volatile, natural and synthetic oils. Among silicone oils those can be added to the pre-treatment composition include dimethicone, dimethiconol, polydimethylsiloxane, DC fluid ranges from Dow Corning, natural oils such as olive oil, almond oil, avocado oil, weizenkeim oil, ricinus oil and the synthetic oils, such as mineral oil.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula I or II, respectively, $$R_{14}\,CO(OCH_2\,CH_2)_n OH \qquad\qquad \text{formula I}$$

$$R_{14}\,CO(OCH_2\,CH_2)_n OOC\,R_{15} \qquad\qquad \text{formula II}$$

where $R_{14}$ and $R_{15}$ are independent from each other saturated, unsaturated or branched or non-branched alkyl chain with 7 to 21 C atoms and n is typically 2-100.

Conditioners mentioned above can be contained as well in mixture in the compositions of the present invention at a concentration of below 1%, preferably below 0.75% by weight calculated to total composition.

The compositions of present invention can contain one or more organic solvent. Examples are such as ethanol, propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. Concentration of organic solvents in the pre-treatment composition should not exceed 30%, preferably should not exceed 20% by weight, calculated to the total composition.

Application of the pre and/or after treatment composition can be any form which enables effectively and homogeneously bringing the compositions onto hair. Pre-treatment composition can be packed into a bottle with a nozzle, which enables easy application, or with a spray device (pump spray) or with a pump, which enables dispensing the composition in the form of liquid or foam (pump foamer). Composition may also be offered in an aerosol bottle from which the composition is dispensed as foam. In the aerosol form, dispensing as a spray may also find its applications in the daily practice. In the case that aerosol form is preferred, suitable propellant gas or mixtures must be added to the composition to make dispensing in the preferred form possible.

In the following examples are listed on developing (called as well oxidative dyestuffs precursors) and coupling agents which are usually found in oxidative hair coloring compositions. It should be noted that present invention is not limited with those examples and in principal it is applicable with any oxidative dyeing agents known in the state of the art.

Examples to developers are p-phenylenediamines and substituted p-phenylenediamines such as 2,5-diamino-toluene, 2-n-propyl or 2-ethyl-p-phenylenediamine, 2,6-di-methyl-p-phenylene-diamine, 2-(2,5-diaminophenyl) ethanol, 1-amino-4-bis-(2'-hydroxy-ethyl)amino-benzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 2-aminophenol, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, 5-amino salicylic acid and/or 1,2,4-triamino benzene or the water-soluble salts thereof.

Suitable tetraminopyrimidines are in particular 2,4,5,6-tetraminopyrimidine and the lower alkyl derivatives thereof; suitable triaminohydroxypyrimidines are, for example 4-hydroxy-2,5,6-triaminopyrimidine, 2-hydroxy-4,5,6-triaminopyrimidine and 5-hydroxy-2,4,6-triaminopyrimidine; suitable mono- and diamino dihydroxypyrimidines are, for example, 2,6-dihydroxy-4,5-diaminopyrimidine, 2,4-diamino-6-hydroxy-pyrimidine or 4,6-dihydroxy-2,5-diaminopyrimidine or the water-soluble salts thereof; a preferred amino-substituted triazine is 2,4-diamino-1,3,5-triazine.

The hair dyeing compositions can as well comprise one or more coupling substance, which can be selected from resorcinol, 2-methyl resorcinol, 4-chlororesorcinol, 2-amino-4-chlorophenol, 5-amino-4-methoxy-2-methylphenol, 2-aminophenol, 3-aminophenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 3-amino-2-methylamino-6-methoxypyridine, 2-amino-3-hydroxypyridine, 2-dimethyl-amino-5-aminopyridine, 2,6-diaminopyridine, 1,3-diamino-benzene, 1-amino-3-(2'-hydroxyethylamino)benzene, 1-amino-3-[bis(2'-hydroxyethyl) amino]benzene, α-naphthol, 4,6-dichlororesorcinol, 1,3-diamino-toluene, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methydioxy benzene, 2,4-diamino-3-chlorophenol, 5-amino-2-methoxyphenol and/or 1-methoxy-2-amino-4-(2'-hydroxyethyl amino)benzene or the water-soluble salts thereof. However, this shall not exclude the addition of further developing and coupling substances.

The total concentration of the developing substances customarily ranges between about 0.05% and 5%, preferably 0.1% and 4%, in particular 0.25% to 3% by weight, calculated to the total hair dyeing composition (excluding the oxidation agent and pre or after treatment agent), whereby these figures are always related to the proportion of free base.

In the hair dyeing compositions, the coupling substance(s) as reaction partners of the developing substance(s) are present in approximately the same molecular proportions as the developing substances, i.e. in amounts from 0.01% to 5.0%, preferably 0.05% to 4%, in particular 0.1% to 3% by weight, calculated to the total composition (excluding pre- or after-treatment and the oxidizing agent), whereby these figures are always related to the proportion of free base.

The preferred weight proportion of the named developing substances to the coupling substances ranges between about 1:8 to 8:1, preferably about 1:5 to 5:1, in particular 1:2 to 2:1.

If desired, the oxidative colouring compositions can also contain so-called shading agents for precise adjustment of the desired shade, in particular direct-acting dyestuffs.

Such shading agents are, for example, nitro dyestuffs such as HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic Acid, 1,2-Diamino-4-nitrobenzol, 1,4-Diamino-2-nitrobenzol, 3-Nitro-4-aminophenol, 1-Hydroxy-2-amino-3-nitrobenzol, 2-Hydroxyethylpicramic acid, 2-amino-4.6-dinitrophenol, 2-amino-4-nitrophenol, 2-amino-6-chloro-4-nitrophenol, etc., preferably in amounts from about 0.05% to 2.5%, in particular 0.1% to 1% by weight of the dyestuff composition (excluding the oxidizing agent).

Cationic direct dyes as disclosed in the patent applications EP 1166752, EP 1172082 and EP 970684 and as well WO 95/01772 can be contained in the compositions of the present invention.

Examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14 and Basic Yellow 57.

For application, the composition comprising oxidation dyestuff precursor is mixed with an oxidizing agent. The preferred oxidizing agent is hydrogen peroxide, for example in a concentration of 2 to 12% by weight.

However, the use of other peroxides such as urea peroxide and melamine peroxide is also possible.

As an alternative to peroxide oxidation, it is also possible to achieve the oxidation by air, for example, by applying onto the hair a composition comprising an oxidation dyestuff precursor as aerosol foam and leaving to process for about 15 to 20 minutes.

The pH-value of the ready-to-use hair dyeing composition, i.e. after mixing with peroxide, can be in a slightly acidic range, i.e. from 5.5 to 6.9, as well as in the neutral or alkaline range, i.e. between pH 7.1 and 11. The pH of the DHA comprising composition can be in the range of 2 to 11.

According to the present invention the best way of achieving the benefits of the present invention is offering a kit for coloring keratin fibers especially human hair consisting of 3 components as follows a- a composition comprising dihydroxyacetone used as a pre- or after-treatment b- a composition comprising oxidative dyestuff mixture in a cosmetically acceptable medium, and c- a composition comprising at least one oxidizing agent in a cosmetically acceptable medium.

According to the present invention the kit as disclosed above is best suited for using when coloring keratin fibers especially human hair for achieving intensive an homogeneous color results.

In the following, various Examples are used to illustrate the invention.

EXAMPLE 1

| Carrier | |
|---|---|
| Stearyl alcohol | 8.0 (% by wt.) |
| Coco fatty acid monoethanolamide | 4.5 |
| 1.2-Propanediol mono/distearate | 1.3 |
| Coco fatty alcohol polyglycolether | 4.0 |
| Sodium lauryl sulfate | 1.0 |
| Oleic acid | 2.0 |
| 1.2-Propanediol | 1.5 |
| Na-EDTA | 0.5 |
| Sodium sulfite | 1.0 |
| Protein hydrolyzate | 0.5 |
| Ascorbic acid | 0.2 |
| Perfume | 0.4 |
| Ammonia, 25% | 1.0 |
| Ammonium chloride | 0.5 |
| Panthenol | 0.8 |
| Water | ad 100.00 |

The oxidation dyestuff combinations were incorporated into this carrier, whereby the water content was reduced accordingly. The following oxidation dyestuff composition is used.

Dyestuff Mixture

| | |
|---|---|
| p-amino-o-cresol | 0.56% by weight |
| 1-hydroxyethyl-4,5-diamino pyrazol sulfate | 0.11% by weight |

In the case that the coloring compositions contained for the comparative purposes DHA, this was as well added to the above carrier compositions and water amount is reduced consequently.

The tests were carried out in all cases on wool patches and switches of bleached human hair. The coloring compositions is obtained after mixing the above given composition comprising dyestuff precursors with oxidizing agent comprising 6% by weight hydrogen peroxide at a mixing ratio of 1:1 by weight. The pH of the resulting mixture was 9.8.

For demonstration of the effects of the invention, the following pre-treatment composition is used.

Pre-treatment Composition

| | |
|---|---|
| Dihydroxyacetone | 0.5% by weight |
| Deminarilized water | 95.5% by weight |

Coloring Tests

Coloring tests were carried out using wool patches and bleached human hair switches. The test was done in 3 different sets to show the effect of the invention.

1—No DHA is added into coloring composition—In this case, 1:1 mixture of coloring composition as given above with example 1 carrier with dyestuff composition and oxidizing agent with 6% by weight hydrogen peroxide was prepared (composition does not contain any DHA). Immediately after preparation, the mixture was applied onto patches and switches (Swatch 1), after 5 minute of break the same composition was applied onto another patches and switches (Swatch 2). Again after 5 min of break (in total 10 min) the same composition was applied onto another patches and switches (Swatch 3). This was again repeated after additional 5 min break (in total 15 min) applied the same composition was applied onto another patches and switches (Swatch 4). All patches and switches were rinsed off with water after 30 min processing time and shampooed. After drying, color measurements were carried out with commercially available equipment (Minolta CR-200) in order to determine the difference in colour nature ($\Delta E$) and intensity ($\Delta L$). $\Delta E$ values are calculated from the L, a and b values measured before and after coloration.

2—0.2% DHA by weight is incorporated into dyestuff composition (without oxidizing agent)—In this case, 1:1 mixture of coloring composition comprising 0.2% by weight DHA as given above with example 1 carrier with dyestuff composition and oxidizing agent with 6% by weight hydrogen peroxide was prepared. Immediately after preparation, the mixture was applied onto patches and switches (Swatch 1), after 5 minute of break the same composition was applied onto another patches and switches (Swatch 2). Again after 5 min of break (in total 10 min) the same composition was applied onto another patches and switches (Swatch 3). This was again repeated after additional 5 min break (in total 15 min) applied the same composition was applied onto another patches and switches (Swatch 4). All patches and switches were rinsed off with water after 30 min processing time and shampooed. After drying, color measurements were carried out with commercially available equipment (Minolta CR-200) in order to determine the difference in colour nature ($\Delta E$) and intensity ($\Delta L$). Delta E values are calculated from the L, a and b values measured before and after coloration.

3—Pre-treatment composition as given above is used in the coloring process—In this case, 1:1 mixture of coloring composition as given above with example 1 carrier with dyestuff composition and oxidizing agent with 6% by weight hydrogen peroxide was prepared (composition does not contain any DHA). Immediately after preparation, the mixture was applied onto patches and switches (Swatch 1), after 5 minute of break the same composition was applied onto another patches and switches (Swatch 2). Again after 5 min of break (in total 10 min) the same composition was applied onto another patches and switches (Swatch 3). This was again repeated after additional 5 min break (in total 15 min) applied the same composition was applied onto another patches and switches (Swatch 4). All patches and switches were rinsed off with water after 30 min processing time and shampooed. After drying, color measurements were carried out with commercially available equipment (Minolta CR-200) in order to determine the difference in colour nature ($\Delta E$) and intensity ($\Delta L$). Delta E values are calculated from the L, a and b values measured before and after coloration.

Results are Presented in Table I.

TABLE I

Results of color measurements and color differences
(bleached human hair switches)

|  | Swatch | L | a | b | ΔE1 | ΔE2 | ΔL1 | ΔL2 |
|---|---|---|---|---|---|---|---|---|
|  | Unterated | 84.28 | 0.76 | 7.06 | — | — | — | — |
| Colored | 1 | 46.76 | 46.76 | 36.42 | 66.23 | 0.00 | 37.52 | 0.00 |
| without DHA | 2 | 45.97 | 46.86 | 36.53 | 66.79 | 0.80 | 38.31 | 0.79 |
| (Set - 1) | 3 | 43.41 | 47.70 | 36.85 | 69.00 | 3.51 | 40.87 | 3.35 |
|  | 4 | 42.90 | 48.80 | 37.79 | 70.46 | 4.58 | 41.81 | 3.86 |
| Colored with DHA | 1 | 47.22 | 46.66 | 36.01 | 65.71 | 0.00 | 37.06 | 0.00 |
| in color mass | 2 | 43.00 | 47.19 | 34.32 | 67.84 | 4.58 | 41.28 | 4.22 |
| (Set - 2) | 3 | 39.50 | 47.10 | 33.25 | 69.56 | 8.21 | 44.78 | 7.72 |
|  | 4 | 36.84 | 47.46 | 33.80 | 71.74 | 10.64 | 47.44 | 10.38 |
| Colored with DHA | 1 | 40.28 | 48.13 | 36.23 | 70.93 | 0.00 | 44.00 | 0.00 |
| as a pre-treatment | 2 | 39.98 | 47.64 | 35.02 | 70.30 | 1.34 | 44.30 | 0.30 |
| (Set - 3) | 3 | 39.43 | 47.98 | 35.66 | 71.13 | 1.03 | 44.85 | 0.85 |
|  | 4 | 39.37 | 48.12 | 35.92 | 71.36 | 0.96 | 44.91 | 0.91 |

For explanation of swatch numbers please refer to the text above.

The ΔE1 value represents the color difference between colored swatches and uncolored bleached human hair swatches.

Similarly ΔL1 value represents the color intensity difference between colored swatches and uncolored bleached human hair swatches.

The ΔE2 value represents the color difference between swatch 1 and swatches 2 to 4 for testing completion of coloration and homogeneity of colorations between the swatches.

Similarly ΔL1 value represents the color intensity difference between swatch 1 and swatches 2 to 4 for testing completion of coloration and homogeneity of color intensity between the swatches.

From the results it is obvious that there is a little color difference among the swatches in the absence of DHA (swatches of Set 1). On contrary, in the presence of DHA in the coloring mass the difference is becoming more and more obvious going from Swatch 1 to Swatch 4 (swatches of Set 2). In the case of Swatch 4 there is a difference to swatch 1 in ΔE2 value of 10.64 (color difference) and in ΔL2 value there is a difference of 10.38 (intensity difference). This shows clearly the application time is importantly effects the color results.

However in the 3rd run (Set 3) where DHA is used as a pretreatment the differences are so small which cannot be seen representing a statistically significant difference.

From these results it is clear that when DHA is used as a pre-treatment homogeneous coloration can be obtained in contrast to its use as an aid in the coloration mixture. In addition, the color and intensity is reached in a much shorter time than compared to the composition not comprising DHA.

EXAMPLES 2-9

Oxidative Dyestuff Compositions

The same results are observed with the following dyestuff compositions.

|  | 2 | 3 | 4 | 5 | 6 | 7 | 8 | 9 |
|---|---|---|---|---|---|---|---|---|
| 4-Hydroxy-2.5.6-tetraaminopyrimidine sulfate | 0.61 | 0.61 | 0.61 |  |  |  |  |  |
| 2.4.5.6-Tetraaminopyrimidine sulfate |  |  |  | 0.53 | 0.53 |  |  | 0.77 |
| 2.4-Diamino-6-hydroxypyrimidine |  |  |  |  |  | 0.28 | 0.28 |  |
| m-Aminophenol |  | 0.25 |  |  |  |  |  |  |
| 2-Methyl resorcinol |  |  |  | 0.28 | 0.28 |  |  |  |
| 4-Amino-2-hydroxytoluene |  |  |  |  |  | 0.27 | 0.27 | 0.40 |
| 2-Amino-4-hydroxyethyl aminoanisol sulfate |  |  |  |  |  |  | 0.60 |  |
| 1-Naphthol | 0.32 |  |  |  |  |  |  |  |

EXAMPLE 10

Pre-treatment Composition

| Dihydroxyacetone | 1.0% by weight |
|---|---|
| Cetrimonium chloride | 0.5% |
| Citric acid | q.s. to pH 6.0 |
| Preservative, fragrance | q.s |
| Water | to 100 |

With the above composition similar results are observed as in the case of example 1.

EXAMPLE 11

Pre-treatment Composition

| | |
|---|---|
| Dihydroxyacetone | 1.0% by weight |
| Hydroxyethylcellulose | 0.3 |
| Citric acid | q.s. to pH 6.0 |
| Preservative, fragrance | q.s |
| Water | to 100 |

With the above composition similar results are observed as in the case of example 1.

EXAMPLE 12

Pre-treatment Composition

| | |
|---|---|
| Dihydroxyacetone | 1.0% by weight |
| Polymer JR 400 | 0.3% |
| Citric acid | q.s. to pH 6.0 |
| Preservative, fragrance | q.s |
| Water | to 100 |

With the above composition similar results are observed as in the case of example 1.

EXAMPLE 13

Pre-treatment Composition

| | |
|---|---|
| Dihydroxyacetone | 1.0% by weight |
| Jaguar C13S | 0.3% |
| Citric acid | q.s. to pH 6.0 |
| Preservative, fragrance | q.s |
| Water | to 100 |

With the above composition similar results are observed as in the case of example 1.

EXAMPLE 14

Pre-treatment Composition in Aerosol Form

| | |
|---|---|
| Dihydroxyacetone | 1.0% by weight |
| Cocamidopropyl betaine | 0.3% |
| Ethanol | 10.0 |
| Preservative, fragrance | q.s |
| Water | to 100 |

The above composition is filled into aerosol cans with 30% dimethylether a gas. The composition is poured as foam directly on the application site. Spraying the same composition gave as well satisfactory results.

The invention claimed is:

1. Process for coloring hair, comprising the steps of:
   forming a first composition by mixing at least one oxidation dye precursor and optionally at least one coupling agent with a composition comprising at least one oxidizing agent, and applying the first composition to the hair,
   and applying a second composition comprising a color intensifying composition consisting of dihydroxyacetone onto the hair either before or after application of the first composition, and
   after allowing the first composition and second composition to remain on the hair for 5 to 45 min, rinsing the compositions off with water.

2. Process according to claim 1, wherein the second composition additionally comprises at least one surfactant selected from anionic, nonionic, cationic and amphoteric ones.

3. Process according to claim 1, wherein the second composition additionally comprises at least one polymer selected from anionic, nonionic, cationic and amphoteric ones.

4. Process according to claim 1, wherein the second composition additionally comprises at least one conditioning agent.

5. Process according to claim 1, wherein the second composition additionally comprises at least one organic solvent.

6. Process according to claim 1, wherein the second compostion has a viscosity of maximum 2000 mPa.s as measured with a Brookfield and/or Höppler viscosimeters at 20° C.

7. Process for coloring hair according to claim 1 characterized in that the concentration of dihydroxyacetone in the second composition is between 0.1 and 20% by weight.

8. Kit for coloring keratin fibers comprising the following:
   a- a composition comprising dihydroxyacetone for use as a pre- or after-treatment
   b- a composition comprising oxidative dyestuff mixture in a cosmetically acceptable medium, and
   c- a composition comprising at least one oxidizing agent in a cosmetically acceptable medium.

\* \* \* \* \*